United States Patent [19]
Conrads et al.

[11] Patent Number: 6,109,097
[45] Date of Patent: Aug. 29, 2000

[54] METHOD OF DETERMINING THE FLOW RATE OF SOLID OR LIQUID MATERIAL IN A GASEOUS MEDIUM OF A TWO-PHASE FLOW

[75] Inventors: Hans Georg Conrads, Barleben; Volkhard Klupsch, Erfurt, both of Germany

[73] Assignee: PROMECON Prozess- und Messtechnik Conrads GmbH, Barleben, Germany

[21] Appl. No.: 09/110,908

[22] Filed: Jul. 6, 1998

[30] Foreign Application Priority Data

Jul. 4, 1997 [DE] Germany ............... 197 28 612

[51] Int. Cl.$^7$ ................................................. G01N 33/00
[52] U.S. Cl. .......................................................... 73/61.41
[58] Field of Search ............................. 73/61 R, 61.41, 73/61.43, 61.44, 861.04, 861.21; 324/58.5 A, 637; 364/510; 435/173; 110/186

[56] References Cited

U.S. PATENT DOCUMENTS

| | | | |
|---|---|---|---|
| 3,710,615 | 1/1973 | Johnson et al. | 73/61 R |
| 4,301,400 | 11/1981 | Paap | 324/58.5 A |
| 4,357,603 | 11/1982 | Roach et al. | 73/861.21 |
| 4,423,623 | 1/1984 | Ho et al. | 73/61 R |
| 4,628,830 | 12/1986 | Kozlak | 110/186 |
| 4,658,208 | 4/1987 | Lee et al. | 73/61 R |
| 4,745,353 | 5/1988 | Stewart et al. | 73/61 R |
| 4,764,718 | 8/1988 | Revus et al. | 324/58.5 A |
| 5,103,181 | 4/1992 | Gaisford et al. | 324/637 |
| 5,120,648 | 6/1992 | Lim et al. | 435/173 |
| 5,121,629 | 6/1992 | Alba | 73/61.41 |
| 5,132,917 | 7/1992 | Baas | 364/510 |
| 5,177,444 | 1/1993 | Cutmore | 324/637 |
| 5,383,353 | 1/1995 | Marelli et al. | 73/61.43 |
| 5,485,743 | 1/1996 | Taherian et al. | 73/61.44 |

FOREIGN PATENT DOCUMENTS

| | | | |
|---|---|---|---|
| 0268399 | 5/1988 | European Pat. Off. | G01N 22/00 |
| 3317215 | 11/1983 | Germany | G01N 22/00 |
| 3316328 | 12/1983 | Germany | G01N 22/00 |
| 3627966 | 8/1987 | Germany | G01N 22/00 |
| 4206532 | 9/1993 | Germany | G01N 22/00 |
| 4426280 | 2/1996 | Germany | G01N 22/00 |
| 58-151517 | 9/1983 | Japan | G01F 1/74 |
| WO 91/05243 | 4/1991 | WIPO | G01N 22/00 |

*Primary Examiner*—William Oen
*Attorney, Agent, or Firm*—Karl Hormann

[57] ABSTRACT

A method of determining the quantity of particulate matter suspended in a carrier gas in a pipe by measuring the frequency shift over a substantially linear range of an attenuation curve below the cut-off frequency for wave propagation, the curve being derived from measuring the attenuation of an electric field established in a conductive pipe substantially free of wave propagation.

26 Claims, 3 Drawing Sheets

METHOD OF DETERMINING THE FLOW RATE OF SOLID OR LIQUID MATERIAL IN A GASEOUS MEDIUM OF A TWO-PHASE FLOW

BACKGROUND OF THE INVENTION

1. Field of the Invention

The invention, in general, relates to a novel method of determining the quanity of solid or liquid particulate matter suspended in a gaseous carrier medium of a two-phase flow and, more particularly, to a method of determining the quanity and quantitative distribution of pulverized coal in a gaseous carrier medium of a pneumatic feed pipe system.

2. The State of the Art

The transportation of minute particles of solid materials or droplets of liquid, hereinafter sometimes referred to a particulate matter, in a gaseous carrier medium of a two-phase flow often necessitates turbulent flows to ensure a sufficient transport velocity and a sufficient quantity of the particulate matter. In transporting particulate matter, in particular pulverized coal, through burner feed pipes of coal-burning power stations, for instance, it has been practically impossible to prevent the formation of so-called ropes. These are sections in the flow pattern of increased density of the particulate matter, i.e., pulverized coal. Ropes may be geometrically stable and localized; but they may also occur stochastically at different positions, and they may change their dimensions and density and migrate within a feed pipe. At splitter boxes in particular, ropes are likely to cause highly irregular distributions of particulate matter and therefore lead to significant differences in the quantities of particulate matter transported within individual feed pipes. It has not only been very difficult to determine the quantity or flow rate of particulate matter transported in pneumatic feed systems, in particular multiple-branch ones, but also to ensure a uniform quantitative cross-sectional distribution of such matter within feed pipes of the kind here under consideration.

Known systems, such as those utilizing tubes for isokinetically withdrawing samples, for instance, often yield strongly distorted results, for they can only detect ropes by chance or, more likely, not at all. Furthermore, such measurements are extremely time-consuming, and as a rule may take hours to deliver results. They are, therefore, by and large useless for closed-loop controls.

For the control of pneumatic feeder systems and for regulating the flow of particulate matter through multiple-branch systems, quickly responding measuring systems are of the utmost importance. For that reason, various attempts have been made to utilize microwaves for such measurements. In such systems, microwaves of predetermined frequencies are fed into an elongate section of a pipe set up as a measuring path, and at the end of the measuring path any change in amplitude and phase of the microwave is registered. The principle underlying measurements with microwaves is that charging or loading a carrier gas with pulverized solids and/or aerosolized liquids changes the complex dielectric constant within the feed pipe and that the microwaves are subject to attenuation and phase shifting as a function of the dielectric constant.

Such methods have been generally disclosed, for instance, by European Patent 0,717,269 and U.S. Pat. No. 5,177,444. However, for pneumatic feed systems, neither sensitivity nor precision of known methods utilizing microwaves are sufficient, especially where the flow rates of a given material differ in individual pipes or pipe sections of multiple-branch feed pipes, or where significant differences in local or homogeneous distribution and volumetric concentration of the particulate matter are encountered within a pipe system in consequence of the mentioned rope formation.

U.S. Pat. No. 4,423,623 describes a microwave measurement system for measuring coal slurries. In coal slurries, microwaves are subject to strong attenuations, and the sensitivity required for measuring coal in water is orders of magnitude lower than the sensitivity required for measuring pulverized coal in a gaseous carrier medium. Ideally, an adequately precise regulation of pulverized coal fed to the burner system of a power plant boiler does not only require a measuring sensitivity or responsiveness in the order of 1 g of coal dust per cubic meter of carrier gas but also a response time in the millisecond range. However, such small load deviations result in extremely small changes of the complex dielectric constant, and their effect on the attenuation and phase of a microwave is very small indeed.

Moreover, the use of microwaves for measuring loads in pneumatic transport systems leads to significant problems because of disturbances caused by reflected microwaves. The attenuation of microwaves is particularly small at low loads, so that analogous to waveguides they propagate in a pipe system over large distances and are reflected by constrictions, splitter boxes, ends of pipes and the like. This may lead to superposed waves propagating to and fro and, consequently, to significant distortions of the results of measurements.

The known methods utilizing microwaves suffer from the further disadvantage of requiring considerable and complex equipment. Usually, an existing feeder pipe system has to be fitted with a pipe section of highly precise geometry to provide a measuring path as well as with complementary transmitting and receiving antennae. Other known methods include the complex mounting of slotted couplers as transmitting and receiving devices in existing pipe sections satisfying predetermined geometric requirements.

OBJECTS OF THE INVENTION

It is a primary object of the invention to provide a method of providing accurate and reliable values of the quantity of particulate matter contained in a gaseous carrier medium of a two-phase pneumatic transport system.

It is also an object of the invention to provide a method of providing accurate and reliable values of the concentration of particulate matter suspended in a gaseous carrier medium of a two-phase pneumatic transport system.

It is a further object of the invention to provide a method of providing accurate and reliable values of the distribution of particulate matter suspended in a gaseous carrier medium of a two-phase pneumatic transport system.

Another object of the invention is to provide a method of the kind referred to which may be implemented by relatively simple means.

A still further object of the invention is to provide a method of the kind referred to which may be practiced without necessitating significant modifications of existing feed ducts.

A more particular object of the invention is to provide a method of quickly yielding accurate results of the flow pattern of particulate matter suspended in a gaseous carrier medium in industrial grade feeder pipes.

It is also an object of the invention to provide a method of measuring very small deviations in the quantity of particulate matter suspended in a gaseous carrier medium of a pneumatic feed system.

A still further object of the invention is to provide a method of determining the quantity of particulate matter suspended in a gaseous carrier medium of a two-phase transport system by setting up, at a first position of a conductive pipe, at least one electric alternating field substantially free of propagating waves and by measuring, at an axially remote second position, the attenuation and frequency shift of the alternating electric field to derive therefrom a value representative of the quantity of suspended particulate matter.

Other objects will in part be obvious and will in part appear hereinafter.

SUMMARY OF THE INVENTION

The invention, in a first advantageous embodiment thereof, provides for a method of the kind referred to, by establishing at least one electric alternating field substantially free of propagating waves from a first position of an electrically conductive measuring section of a pipe system supporting a two-phase flow and measuring, at a second position which is axially displaced from the first position, any attenuation as a function of frequency of the electric alternating field, initially recording the attenuation as a function of frequency of the electric alternating field in respect of a load including a known quantity of particulate matter over the measuring section for determining the parameters of the section, defining and storing as a reference value a substantially linear range in the area of the steepest slope of the curve of the measured attenuation intermediate an upper attenuation threshold value with an associated lower frequency and a lower attenuation threshold value with an associated higher frequency, and determining, by means of a predetermined measuring process, the frequency shift over the substantially linear range to derive therefrom a value representative of the quantity of solids in the two-phase flow.

The invention draws upon the fact that below the characteristic cut-off frequency of wave propagation the relationship between frequency and attenuation of an electric alternating field over a constant path experiences, in a manner similar to a step function, a relatively steep and almost linear transition from a high value of attenuation to a low value of attenuation. The shape of this transition (step function) between a non-loaded state in which no particulate matter is suspended in the carrier gas and a relatively high load remains substantially unchanged, but the frequency range within which this transition lies shifts as a function of the load in the direction of lower frequencies, the extent to which the frequency shifts being a measure of the quantity of particulate matter in the carrier gas.

The essence of the invention resides in establishing an electric alternating field within an elongate section of a pipe system and to measure the attenuation of electric alternating the field over a path of predetermined length. It does not matter whether the path extends in the direction of flow or against it. Initially, shape and frequency range of the transition may be determined in an unloaded state. Thereafter, the frequency shift of the transition toward lower frequencies resulting from a load is determined on the basis of known relationships to derive therefrom the quantity of particulate matter supported by the carrier gas. For practical purposes, a substantially linear range is defined within the transition. The substantially linear range is limited by an upper attenuation value associated with a low frequency and a lower attenuation value associated with a high frequency. Within this substantially linear range, the attenuation curve has a point of inflection above the frequency. The point of inflection may mathematically and technically easily be determined. It is within this substantially linear range that small frequency changes are related to large attenuations of the electric alternating field so that within this substantially linear range points or ranges may be detected or determined with great exactitude.

As will hereafter appear, the invention may be practiced in connection with various embodiments.

For instance, a characteristic value of attenuation and associated frequency may initially be selected in an unloaded state from within the substantially linear range, and for determining a load the frequency of the established electric alternating field may be changed (increased) commencing with a predetermined starting frequency until the attenuation measured in the loaded state equals the initially selected one. For practical purposes, the starting frequency should be lower, but in no case higher, than the low frequency of the substantially linear range at the probable maximum load of any given application. The starting frequency may be determined by subtracting from the low frequency of the substantially linear range in the non-loaded state the frequency shift $\Delta f$ resulting from a maximum load. The frequency shift $\Delta f$ may be easily calculated by the following equation:

$$\Delta f = f_0 \left(1 - 1/\sqrt{\mu_r \varepsilon_r}\right) \quad (1)$$

wherein $f_0$ is the cut-off frequency of the pipe system in a non-loaded state, $\mu_r$ is the relative magnetic permeability and $\varepsilon_r$ is the relative dielectric constant of the mixed carrier medium and particulate material.

Accordingly, the difference between the frequencies corresponding to the selected characteristic attenuation value in the loaded and non-loaded states is a measure of the load.

It will be understood by those skilled in the art that the selected attenuation should lie within the steepest, i.e. substantially linear range so that the method can attain its maximum sensitivity. For practical reasons the point of inflection of the attenuation curve would be preferred.

To accelerate the measuring process, it has been found to be useful, commencing at the mentioned starting frequency, to increase the frequency in steps derivable from the difference between the high and low frequencies of the substantially linear range, until the measured attenuation lies within the substantially linear range. As mentioned before, the difference between the frequency corresponding to the attenuation measured in the non-loaded state and the measured frequency constitutes a measure of the load.

Of course, applying the straight-line equation describing the substantially linear range, the measured attenuation within the substantially linear range and its associated frequency may be converted to a different selected characteristic attenuation value to define the frequency shift of this characteristic attenuation value between a non-loaded to a loaded state.

One of the important advantages of the method in accordance with the invention is that in contrast to known microwave systems the measuring path along which the attenuation of the electric alternating field is measured need not satisfy any extreme tolerances as regards the roundness of the pipe. Measurements may be taken in pipes corresponding to common industrial specifications or standards, such as A.S.A or DIN. Even with such pipes the sensitivity of the method responding to <1 g of solids per cubic meter of gas is remarkably good.

A further advantage of the method is that the electric alternating field is set up by short mismatched antennae. Since the transmitting and receiving antennae are similarly structured, abrasions do not affect the sensitivity of the measuring process in any significant way and wear-induced replacements of the antennae are only infrequently required. Moreover, short antennae may easily be mounted into existing pipe systems.

The invention may also be advantageously applied whenever ropes are formed within a pipe system. For detecting and measuring a rope, two electric alternating fields are established which are preferably of identical frequency and phase but azimuthally displaced from each other by 90°, and the frequency shift over the substantially linear range of the attenuation curve of both of these electric alternating fields over a predetermined measuring path is determined in the manner described above.

In one embodiment of the invention the alternating electric fields which are azimuthally displaced 90° from each other are established sequentially or alternatingly, and the frequency shift over the substantially linear range of the attenuation curves is determined by receiving antennae which are also azimuthally displaced from each other by 90° and which lie in the same axial planes as the respective transmitting antennae. A rope will cause the frequency shifts of the attenuation curves of the azimuthally displaced electric alternating fields to be different from each other. By forming average values until additional measurements yield no further significantly different results, a frequency shift will result which corresponds to the average load density including the rope.

It is, however, also possible by the method in accordance with the invention to determine the spatial position and the intensity of a rope within a pipe. To this end, two phase-locked and linearly polarized electric alternating fields of identical frequencies and azimuthally displaced from each other by 90° are established in the pipe, and the frequency shift over the substantially linear portion of the attenuation curve of these electric alternating fields is measured over a predetermined measuring path. The two fields are established simultaneously and combined into a resultant new field which is linearly polarized provided the phase between the two fields equals n×180°, wherein n is a whole integer. Hence, the resultant frequency shift over the substantially linear portion of the attenuation curve is a measure of a load in an azimuthal direction of the resultant electric alternating field. By varying the amplitudes of the electric alternating fields displaced by 90° azimuth, the resultant alternating field may be azimuthally rotated. Preferably, the amplitude of the resultant alternating field should be kept constant. The maximum and minimum frequency shifts of the substantially linear portion of the attenuation curve are determined by azimuthal rotation of the resultant alternating field. If a rope is present, the maximum and minimum frequency shifts will be azimuthally displaced by 90°. The location of a rope may be calculated on the basis of associated azimuthal directions. But the result will be ambiguous since the electric alternating field is axially symmetric. Accordingly, at a maximum frequency shift the azimuthal disposition of the electric alternating field will relate to the azimuthal location of the rope in the following way: $\alpha_{St}=\alpha_F+n\times180°$, wherein $\alpha_{St}$=the azimuthal angle of the rope, $\alpha_F$=the azimuthal angle of the electric alternating field and n is a whole number. A rope detected in this manner may thus always be located in two quadrants disposed mirror symmetrically of each other.

The ratio of the maximum and minimum field strengths permeating the rope may be determined directly from the ratio of maximum and minimum frequency shifts. The radial location of a rope may be defined on the basis of the known quantitative field strength distribution of the electric alternating field within the pipe.

In order to provide an unambiguous azimuthal localization of a rope it is necessary by a further process step to determine that half of the cross-section of the pipe within which the rope is located. In accordance with the invention, this may be accomplished by evaluating an alternating voltage induced in a receiving antenna which is azimuthally displaced from the transmitting antenna by 90°. If the azimuthal position of the transmitting antenna is assumed to be 0°, the electric alternating field at the 180° position will be of the same field strength but of inverse polarity. Given a homogeneous load, the electric field strength and, hence, the alternating voltage induced in the receiving antenna will be zero at the 90° position. If a rope is present in that half section of the pipe in which the transmitting antenna is located the electric field will be distorted such that an electric field of the same intensity but of opposite polarity will be detected at the receiving antenna which is azimuthally displaced by 90° relative to the transmitting antenna. This induces an electric alternating voltage of a phase opposite to the alternating voltage energizing the transmitting antenna. If the rope is present in the semi-section of the pipe opposite from the transmitting antenna the phase of the voltage at transmitting and receiving antennae will be identical. Advantageously, this measurement is repeated by reversing transmitting and receiving antennae so that even ropes positioned in the immediate vicinity of transmitting and receiving antennae may be detected with sufficient certainty.

Moreover, the velocity of movement of the matter being transported may be measured by the method in accordance with the invention. To this end, the fluctuations over time in the load density inherent in the turbulent flow are registered at two positions which are axially displaced from the position from which the electric alternating field is established, and the difference in time of the two paths is evaluated by a correlation filter. Preferably, one of these positions is positioned upstream and the other one is positioned downstream of the position from which the electric alternating field is established. The velocity of movement of the transported matter may be derived from the difference in time and the distance between the upstream and downstream positions. The flow rate may be derived from the average density of the matter and from the velocity of movement.

BRIEF DESCRIPTION OF THE SEVERAL DRAWINGS

The novel features which are considered to be characteristic of the invention are set forth with particularity in the appended claims. The invention itself, however, in respect of its structure, construction and lay-out, as well as manufacturing techniques, together with other objects and advantages thereof, will best be understood from the following description of preferred embodiment when read with reference to the appended drawings, in which:

DETAILED DESCRIPTION OF PREFERRED EMBODIMENTS

In the context of the disclosure the term "particulate matter" is intended in general to connote particles of solid or droplets of liquid substances and pulverized coal in particular, and "two-phase flow" is intended to connote the transport of one or both such substances suspended in a carrier gas for purposes of transportation, hereinafter sometimes referred to as "pneumatic transportation", through a pipe.

The general task underlying the present invention is to determine the quantity or rate of flow of pulverized coal pneumatically transported in a burner feed pipe 1 of a coal-fired power plant and to detect the presence of possible roping within the pipe. The pipe 1 schematically shown in FIG. 1 may be of circular cross-section with a nominal internal diameter of 500 mm, for instance, and its temperature may be assumed to be substantially uniform over extended periods of time.

Figure 1:
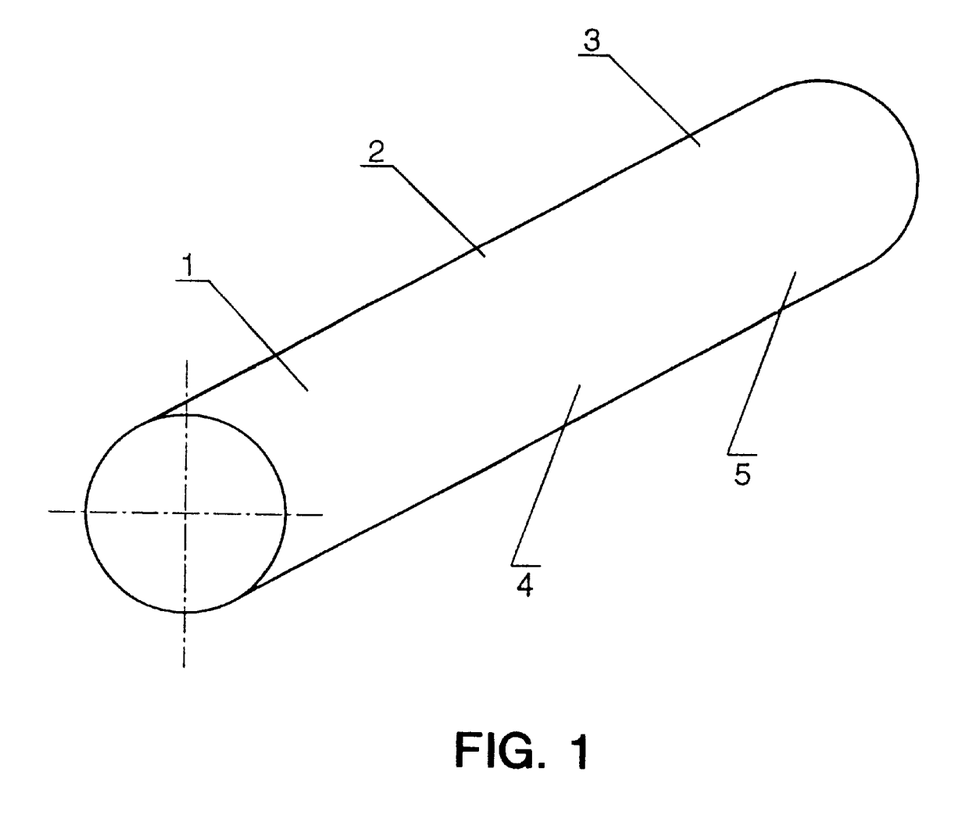
FIG. 1 is a schematic view in perspective of a section of a burner feed pipe of a coal-fired power plant.

Initially, two bores are drilled through the wall of a substantially straight section of the pipe 1. The bores are axially aligned and are placed 1,000 mm apart from each other. A short antenna with an axial dimension of about 5 cm is inserted into each bore. For this purpose, coaxial mismatched structures have been found to be particularly useful. The use of such antennae has been found to be particularly advantageous because not only are they subject to very little mechanical wear but also because any wear has but a negligible effect upon the sensitivity of the electrical system. The first antenna 2, seen in the flow direction of the coal-air mixture, is used as a transmitter, and the second antenna 3 is used as a receiver. With a view to suppressing propagating harmonics in the pipe a steep-skirted discrimination filter is connected to the input of each antenna. The cut-off frequency of these filters is only slightly higher than the cut-off frequency of the feed pipe 1. The transmitting antennae may be energized by conventional high powered generators (not shown) of high spectral purity.

Figure 2:
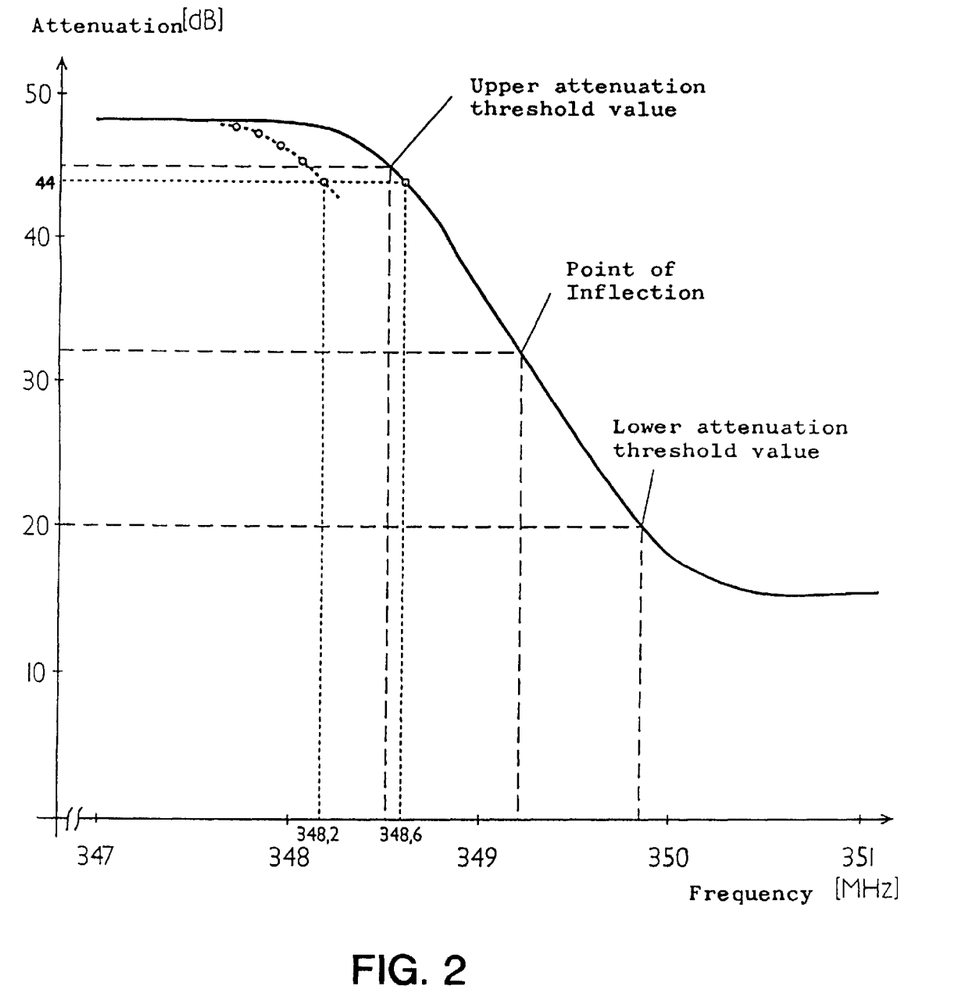
FIG. 2 is a curve depicting an attenuation as a function of frequency in the range of the steep transition from a high attenuation to low attenuation.

To determine the parameters of the measuring path of the feed pipe 1, the attenuation as a function of frequency of an electric alternating field along the measuring path is initially determined. To this end, an electric alternating field substantially free of propagating waves is established in the boiler feed pipe 1 when in a non-loaded state, by way of the transmitting antenna 2, and the attenuation of the electric alternating field as a function of frequency is normatively measured at the receiving antenna 3. As shown in FIG. 2, the result is a curve with a typical slope in which the attenuation drops relatively steeply and substantially linearly within a frequency range of about 1.3 MHz. A substantially linear reference range is then defined within the range of transition between the high and low attenuations. The reference range is positioned between an upper attenuation threshold value of about 45 dB at a low frequency of about 348.5 MHz and a lower attenuation threshold value of about 20 dB associated with a high frequency of about 349.8 MHz. Within this reference range the point of inflection of the attenuation curve is positioned at a frequency of about 349.3 MHz and an attenuation of about 32 dB.

The steepest drop of the attenuation curve occurs within this substantially linear range. That is to say, at a constant measuring frequency small changes in a load result in large changes in attenuation.

The absolute values of the upper and lower attenuation threshold values are dependent upon the strength of the established electric alternating field and upon the sensitivity of a receiver. In FIG. 2, the cut-off frequency below which no wave propagation can occur is indicated at about 350 MHz.

In an actual application, the maximum load of pulverized coal may be assumed to be 1,500 g per cubic meter of air. The resultant relative dielectric constant of the coal-air mixture is $\epsilon_r=1.003$. The relative magnetic permeability $\mu_r$ is approximately 1. Based upon the equation $$\Delta f = f_0\left(1 - 1/\sqrt{\mu_r \varepsilon_r}\right)$$

the resultant frequency is approximately 523 kHz. For determining the quantity of pulverized coal contained in the air current, an electric alternating field of a starting frequency of 347.9 MHz (the low frequency corresponding to the upper attenuation threshold value in the unloaded state minus the change in frequency Δf is established in the loaded state of the pipe by way of the transmitting antenna 2, and its attenuation over the measuring path is detected at the receiving antenna 3. Initially, the attenuation will be above the substantially linear reference range and is then lowered by increasing the frequency of the electric alternating field, for instance incrementally, until its associated attenuation lies within the substantially linear range. The attenuation values detected at different frequencies in a loaded state are diagrammatically shown in FIG. 2 by a dashed line. Thus, for an electric alternating field with a frequency of 348.2 MHz the attenuation has been depicted to be 44 dB. This attenuation lies well within the substantially linear reference range. In the non-loaded state, the same attenuation may be seen to occur at 348.6 MHz. Accordingly, the substantially linear range of the attenuation curve is shifted by 0.4 MHz between loaded and non-loaded states. Based upon the equation $$\Delta f = f_0\left(1 - 1/\sqrt{\mu_r \varepsilon_r}\right),$$

the quantity of pulverized coal in the air flow may be calculated from the frequency shift Δf of the substantially linear range and the changed relative dielectric constant $\epsilon_r$ of the coal-air mixture. The relative permeability $\mu_r$ approximates 1. Accordingly, each cubic meter of air can be calculated to contain 0.16 g of coal. To increase the sensitivity of the method it is useful to select the point of inflection within the substantially linear range as a reference point, and when determining the quantity of pulverized coal within the air current to change the frequency of the electric alternating field until its associated attenuation corresponds to the attenuation at the point of inflection. This is of particular advantage because at the point of inflection the slope of the substantially linear range is at its steepest thus yielding the greatest sensitivity. Care must, however, be exercised in ensuring that the point of inflection lies below the cut-off frequency.

For accelerating the measuring process it is useful, as regards the second measuring point, to increase the starting frequency detected for the maximum load by the difference between the upper and lower frequencies of the substantially linear range. In the instant example it is 1.3 MHz. In this manner a measuring point with an attenuation within the substantially linear range may be established with a minimum number of measurements. The frequency shift over the substantially linear range may either be determined directly on the basis of the measuring point, or the point of inflection in the loaded state is determined on the basis of the straight-line equation of the substantially linear range before the frequency shift over the substantially linear range from the loaded state to the non-loaded state is calculated on the basis of the two inflection points.

For ropes to be included in the result of the measurements, additional transmitting and receiving antennae 4, 5 have to be incorporated in the section of the boiler feed pipe 1. While azimuthally displaced by 90° relative to the transmitting and receiving antennae 2 and 3, the additional antennae 4 and 5 will respectively be positioned in the same axial planes as the antennae 2 and 3.

For determining an average load including a rope, the load of pulverized coal in the air flow is determined in the manner described supra by sequentially or alternatingly generating electric alternating fields between the antennae 2 and 3 and 4 and 5, respectively, and an average value is derived from the two measurements. The rope will thus be included in the average value. By repeating this cycle of forming an average value several times the accuracy of the result of the measurement may be improved. It has been found to be useful to repeat the cycle until the overall average value no longer changes, or changes only negligibly.

While at present linear polarization of the electric alternating fields is preferred in the context of the present invention, those skilled in the art will understand that utilizing circularly polarized phase-locked fields is also possible.

For detecting a rope, linearly polarized and phase-locked (phase of n×180°, wherein n is a natural number) electric alternating fields of identical frequencies are established by way of the transmitting antennae 2 and 4. The fields are combined in the boiler feed pipe 1 to a new resultant electric alternating field. The attenuation of these two electric alternating fields is detected by the receiving antennae 3 and 5, and the attenuation of the resulting electric alternating field over the measuring path can be derived therefrom. By changing the amplitudes of the two electric alternating fields the inclination of the resultant electric alternating field may be azimuthally rotated by up to 90°. By reversing the phase of one electric alternating field the range of rotation of the resultant electric alternating field may be increased to 180°. In the present embodiment utilizing a burner feed pipe 1 of a nominal internal diameter of 500 mm, an electric alternating field with an attenuation of +20 dB (corresponding to a transmission power of about 100 mW) is established in the burner feed pipe 1 by the antennae 2 and 4. To achieve an azimuthal rotation in 22.5° increments of the resultant electric alternating field created by combining the individual alternating fields which are azimuthally displaced by 90°, the feed lines of the antennae are attenuated by the values of the following table:

| azimuthal direction | antenna 2 | antenna 4 |
| --- | --- | --- |
| 0° | 0 dB | −50 dB |
| 22.5° | −1 dB | −9 dB |
| 45° | −3 dB | −3 dB |
| 67.5° | −9 dB | −1 dB |
| 90° | −50 dB | 0 dB |
| 112.5° | −9 dB (180° phase reversal) | −1 dB |
| 135° | −3 dB (180° phase reversal) | −3 dB |
| 157.5° | −1 dB (180° phase reversal) | −9 dB. |

The frequency shift over the substantially linear range is determined at each stated azimuthal direction of the resultant electric alternating field, and on the basis thereof the load of pulverized coal in the air flow is calculated in the aforementioned manner. The detected frequency shifts are listed in the following table:

| azimuthal direction | frequency shift |
| --- | --- |
| 0° | 125 kHz |
| 22.5° | 177 kHz |
| 45° | 200 kHz |
| 67.5° | 266 kHz |
| 90° | 376 kHz |
| 112.5° | 260 kHz |
| 135° | 192 kHz |
| 157.5° | 160 kHz |

Figure 3:
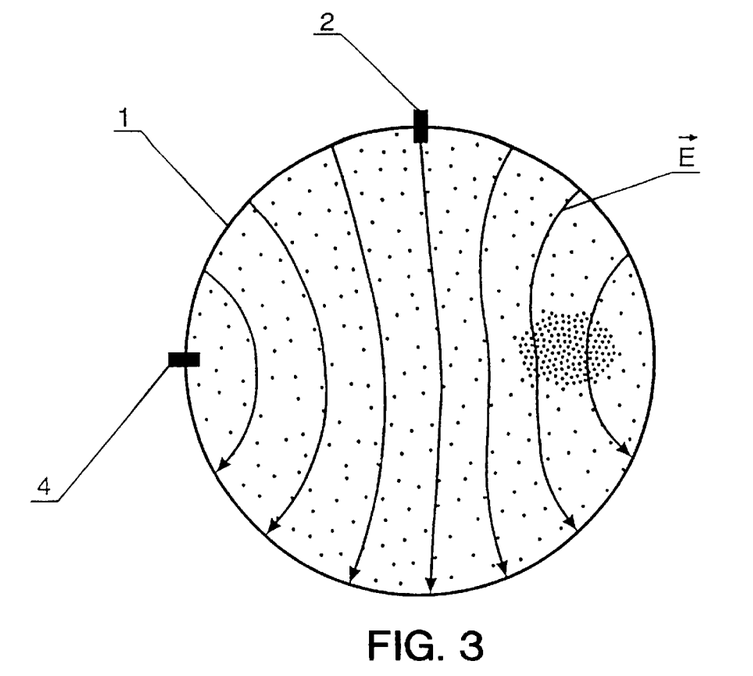
FIG. 3 depicts an electric alternating field resulting in the presence of a rope within the burner feed pipe (azimuthal direction 0°)
Figure 4:
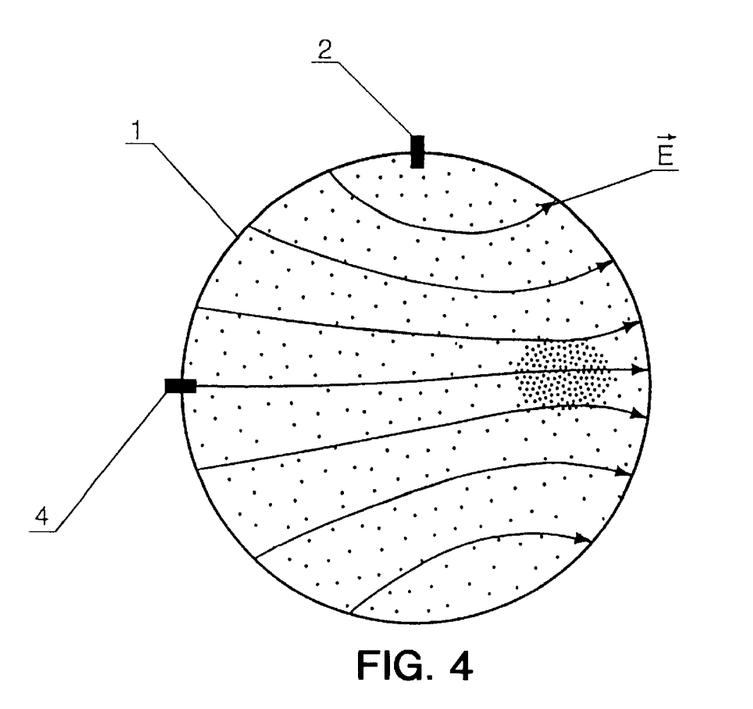
FIG. 4 depicts an electric alternating field resulting in the presence of a rope within the burner pipe (azimuthal direction 90°).

Maximum values can be unambiguously established for the frequency shift and, hence, for the load. This means that a rope must be present in the azimuthal direction of 90°. FIGS. 3 and 4 respectively depict the resulting electric alternating field within the burner feed pipe 1 at the 0° and 90° azimuthal directions.

The radial position of the rope may be deduced from the ratio of maximum (maximum load) and minimum (minimum load) frequency shifts. In the present case, i.e. at a ratio of 1:3, a rope will be positioned closely adjacent to the wall of the pipe. The closer the result approaches 1, the closer the rope will be positioned at center of the pipe. Accordingly, a rope in the true center of the pipe cannot be detected.

Of course, it is only practical to detect ropes which are stationary, i.e. ropes which are quasi stationery relative to a measuring interval. Since the measuring intervals are in the range of a few milliseconds, effective measurements can usually be taken. The purpose of detecting ropes in any event is to eliminate them and in this sense only quasi stationary ropes assume any importance.

It will thus be seen that the invention discloses an effective method of detecting and measuring the quantity and quantitative distribution of articulate matter suspended in a carrier gas of a feed pipe.

What is claimed is:

1. A method of measuring the quantity of particulate matter of known dielectric properties suspended in a gaseous carrier medium for transport in a predetermined direction within a pipe, comprising:

providing in the pipe an electrically conductive measuring path;

establishing from a first position of the measuring path at least one electric alternating field below the characteristic cut-off frequency of wave propagation;

initially measuring, with a predetermined load of particulate matter in the measuring path, any attenuation of the electric alternating field as a function of frequency at a second position of the measuring path axially remote from the first position thereby to determine the parameters of the measuring path;

determining a curve representative of the attenuation of the electric alternating field relative to frequency between the first and second positions;

defining as a reference value a substantially linear range from the steepest slope of the curve between an upper threshold value with an associated low frequency and a lower threshold value with an associated high frequency, and providing an undetermined load of suspended particulate matter in the measuring path;

deriving a value representative of the quantity of particulate matter of the undetermined load by determining the shift in frequency over the substantially linear range.

2. The method of claim 1, further comprising the step of providing a transmitting and a receiving antenna at the first and second positions, respectively.

3. The method of claim 2, wherein the transmitting and receiving antennae are mismatched.

4. The method of claim 3, including the step of energizing the transmitting antenna by a high-power generator of high spectral purity for establishing the electric alternating field.

5. The method of claim 1, further including the steps of:
selecting in the substantially linear range a reference point with an associated attenuation and frequency;
establishing a second electric alternating field at a second frequency lower than the cut-off frequency minus a frequency shift resulting from a maximum load of particulate matter in the carrier medium;
increasing the second frequency until its associated attenuation is equal to the attenuation associated with the reference point;
deriving a difference between the increased lower frequency and the frequency associated with the reference point; and
deriving from the difference the value representative of particulate matter suspended in the carrier medium.

6. The method of claim 5, wherein the lower frequency is increased in increments not exceeding the difference in frequency between the upper and lower threshold values until its associated attenuation lies within the upper and lower threshold values and wherein the frequency is extrapolated to the attenuation associated with the associated reference point.

7. The method of claim 5, wherein the curve has a point of inflection and wherein the substantially linear range is selected to include the point of inflection.

8. The method of claim 7, wherein the point of inflection is selected as the reference point.

9. The method of claim 1, further including the steps of:
measuring fluctuations over time in the load density at a position a predetermined distance downstream from the first position and at another position a predetermined distance upstream from the first position;
evaluating the difference in time over the downstream and upstream positions;
deriving a value of the transport velocity from the difference in time and the distance between the downstream and upstream positions.

10. A method of measuring the flow rate of particulate matter of known dielectric properties transported by a gaseous carrier medium in a pipe, comprising the steps of:
providing in the pipe an electrically conductive measuring path;
alternatingly establishing from a pair of first positions in the measuring path first and second axially coinciding electric alternating fields substantially free of wave propagation and azimuthally displaced from each other by 90°;
measuring with a predetermined load of particulate matter in the measuring path the attenuation of the first and second electrically alternating fields at a pair of second positions axially spaced from the pair first positions and azimuthally displaced from each other by 90°;
determining first and second curves representing the attenuations as a function of frequency between the first and second positions of the first and second electric alternating fields;
defining as reference values substantially linear ranges from the steepest slope of each curve between an upper threshold value having a low frequency associated therewith and a lower threshold value having a high frequency associated therewith;
deriving a value representative of the quantity of particulate matter suspended in the carrier medium by determining the frequency shift over the substantially linear portion of each curve.

11. The method of claim 10, further comprising the step of providing a pair of transmitting and a pair of receiving antenna at the first and second positions, respectively.

12. The method of claim 11, wherein the transmitting and receiving antennae are mismatched.

13. The method of claim 12, including the step of energizing the transmitting antennae by at least one high-power generator of high spectral purity for establishing the electric alternating field.

14. The method of claim 10, further including the steps of:
selecting in the substantially linear range of each curve a reference point with an associated attenuation and frequency;
establishing another pair of electric alternating fields azimuthally displaced 90° from each other at a frequencies lower than the cut-off frequencies minus the frequency shifts ($\Delta f$) at a maximum load of particulate matter in the carrier medium $$(\Delta f = f_0(1 - 1/\sqrt{\mu_r \varepsilon_r}));$$

increasing the lower frequencies until their associated attenuations are equal to the attenuations associated with the reference points;
deriving a difference between the increased lower frequencies and the respective frequencies associated with the reference points; and
deriving from the differences the value representative of particulate matter suspended in the carrier medium.

15. The method of claim 14, wherein the lower frequencies are increased in increments not exceeding the differences in frequencies between the upper and lower threshold values until their associated attenuations lie within the upper and lower threshold values and wherein the frequencies are extrapolated to the attenuations associated with the associated reference points.

16. The method of claim 14, wherein each curve has a point of inflection and wherein the substantially linear ranges are selected to include the respective points of inflection.

17. The method of claim 14, wherein the points of inflection are selected as the reference points.

18. A method of measuring the flow rate of particulate matter of known dielectric properties transported by a gaseous carrier medium in a pipe, comprising the steps of:
providing in the pipe an electrically conductive measuring path;
simultaneously establishing from a pair of first positions in the measuring path first and second phase-locked electric alternating fields of identical frequencies and substantially free of propagating waves and azimuthally displaced from each other by 90°;
combining the first and second electric alternating fields to a new resultant field;

measuring with a predetermined load of particulate matter in the measuring path the attenuation of the new resultant field at a pair of second positions axially spaced from the pair of first positions and azimuthally displaced from each other by 90°;

determining a curve representing the attenuation relative to frequency of the new resultant field between the first and second positions;

defining as a reference value a substantially linear range from the steepest slope of the curve between an upper threshold value having a low frequency associated therewith and a lower threshold value having a high frequency associated therewith;

deriving a value representative of the quantity of particulate matter suspended in the carrier medium by determining the frequency shift over the substantially linear portion of the curve;

rotating the combined electric alternating field in an azimuthal direction by varying the amplitudes of the first and second electric alternating fields and by inverting the phase of one of the fields until maximum and minimum loads of particulate matter have been determined;

deriving from the maximum and minimum loads and their spatial relationship a measure of the total load and an approximate indication within an angular range of 180° of the position and density of a rope in the load.

19. The method of claim 18, further comprising the step of providing a pair of transmitting and a pair of receiving antenna at the first and second positions, respectively.

20. The method of claim 19, wherein the transmitting and receiving antennae are mismatched.

21. The method of claim 20, including the step of energizing the transmitting antennae by at least one high-power generator of high spectral purity for establishing the electric alternating field.

22. The method of claim 18, further including the steps of:

selecting in the substantially linear range of the curve a reference point with an associated attenuation and frequency;

establishing another electric alternating field at a frequencies lower than the cut-off frequencies minus the frequency shift (Δf) at a maximum load of particulate matter in the carrier medium $$(\Delta f = f_0(1 - 1/\sqrt{\mu_r \varepsilon_r}));$$

increasing the lower frequency until its associated attenuation is equal to the attenuation associated with the reference point;

deriving a difference between the increased lower frequency and the frequency associated with the reference point; and deriving from the difference the value representative of particulate matter suspended in the carrier medium.

23. The method of claim 22, wherein the lower frequency is increased in increments not exceeding the difference in frequencies between the upper and lower threshold values until its associated attenuation lies within the upper and lower threshold values and wherein the frequency is extrapolated to the attenuation associated with the associated reference point.

24. The method of claim 22, wherein the curve has a point of inflection and wherein the substantially linear range is selected to include the respective point of inflection.

25. The method of claim 22, wherein the point of inflection is selected as the reference point.

26. The method of claim 18, further including the steps of:

establishing from the first position a further electric alternating field at a frequency within the substantially linear range of the curve;

detecting the further electric alternating field at a remote position azimuthally displaced from the first position by 90°;

defining the position of the rope by the phase position of alternating voltages induced at the remote position, whereby proceeding from the second position at 0° azimuth the rope is located in a range between >90° to <270° in case of phase identity and in the range between >270° and <90° in case of an opposite phase.

* * * * *